(12) United States Patent
Jansen (10) Patent No.: US 9,375,224 B2
(45) Date of Patent: Jun. 28, 2016

(54) DEVICE FOR REMOVING TISSUE

(76) Inventor: Anton Jansen, Heemstede (NL)

(*) Notice: Subject to any disclaimer, the term of this patent is extended or adjusted under 35 U.S.C. 154(b) by 234 days.

(21) Appl. No.: 13/818,610

(22) PCT Filed: Aug. 21, 2011

(86) PCT No.: PCT/NL2011/050570
§ 371 (c)(1),
(2), (4) Date: May 8, 2013

(87) PCT Pub. No.: WO2004/082462
PCT Pub. Date: Sep. 30, 2004

(65) Prior Publication Data
US 2013/0245636 A1    Sep. 19, 2013

(30) Foreign Application Priority Data

Aug. 22, 2010  (NL) ..................................... 1038192
Sep. 16, 2010  (NL) ..................................... 2005359

(51) Int. Cl.
*A61B 17/26* (2006.01)
*A61B 17/221* (2006.01)
*A61B 17/00* (2006.01)

(52) U.S. Cl.
CPC ......... *A61B 17/221* (2013.01); *A61B 17/00234* (2013.01); *A61B 2017/00287* (2013.01)

(58) Field of Classification Search
CPC ...................... A61B 17/221; A61B 2017/2212; A61B 2017/00287
See application file for complete search history.

(56) References Cited

U.S. PATENT DOCUMENTS

| 5,215,521 | A | 6/1993 | Cochran |
| 5,279,539 | A | 1/1994 | Bohan et al. |
| 5,354,303 | A * | 10/1994 | Spaeth ............. A61B 17/00234 604/171 |
| 5,368,597 | A | 11/1994 | Pagedas |
| 5,454,822 | A | 10/1995 | Schob et al. |
| 5,465,731 | A | 11/1995 | Bell et al. |
| 5,480,404 | A | 1/1996 | Kammerer et al. |
| 5,496,259 | A | 3/1996 | Perkins |
| 5,735,289 | A | 4/1998 | Pfeffer et al. |
| 6,228,095 | B1 | 5/2001 | Dennis |
| 6,350,267 | B1 | 2/2002 | Stefanchik |
| 6,887,255 | B2 | 5/2005 | Shimm |
| 7,112,172 | B2 | 9/2006 | Orban, III et al. |
| 7,115,125 | B2 | 10/2006 | Nakao et al. |
| 2005/0267492 | A1 * | 12/2005 | Poncet et al. ................. 606/114 |
| 2006/0052670 | A1 | 3/2006 | Stearns et al. |
| 2007/0016225 | A1 | 1/2007 | Nakao |

FOREIGN PATENT DOCUMENTS

EP    0465051 B1    8/1995
EP    1700569 A1    9/2006

(Continued)

*Primary Examiner* — Ashley Fishback
(74) *Attorney, Agent, or Firm* — Thomas P. O'Connell; O'Connell Law Firm

(57) ABSTRACT

A device for removing tissue by means of laparoscopy or thoracoscopy with an operating part and an optionally partially open hollow tube with a guide for operating a removing part. The removing part has the form of a zeppelin with one or more ribs. The removing part is provided on the upper side with longitudinal connecting elements.

Further described is an application of such a device in a surgical treatment wherein, by use of the operating part, the removing part with the form of a zeppelin is opened out, the removed tissue is collected in the expanded bag of the removing part, and the removing part with tissue is pulled optionally at least partially into the open part of the hollow tube. The connecting elements of the removing part can then be brought together and snapped or zipped closed.

13 Claims, 8 Drawing Sheets

(56) References Cited

FOREIGN PATENT DOCUMENTS

| | | | |
|---|---|---|---|
| EP | 1707130 | B1 | 3/2008 |
| EP | 1700569 | B1 | 11/2008 |
| GB | 2371991 | A | 8/2002 |
| WO | WO9735522 | A1 | 10/1997 |
| WO | WO0135831 | A1 | 5/2001 |
| WO | WO03082122 | A1 | 10/2003 |
| WO | WO2004082462 | A2 | 9/2004 |
| WO | WO2007048078 | A1 | 4/2007 |

* cited by examiner

DEVICE FOR REMOVING TISSUE

FIELD OF THE INVENTION

The invention relates to a device for removing tissue by means of laparoscopy or thoracoscopy and to application thereof during a surgical treatment.

BACKGROUND OF THE INVENTION

When laparoscopic and thoracoscopic surgery is performed, use is frequently made of an extraction apparatus comprising an endo-removal apparatus. For instance, one such extraction apparatus comprises a surgically insertable receptacle that is sold under the registered trademark ENDOBAG by Covidien LP of Mansfield, Mass., USA. That extraction apparatus generally consists of an operating part with a handle, a tubular guide with a trocar, and a removing part. The organ or parts thereof to be removed is collected in this removing part, which is formed, for instance, by a plastic bag so that the spread of malignant or infected cells is prevented. This is described for instance in U.S. Pat. No. 5,480,404. Further, U.S. Pat. No. 5,215,521 describes a removing part that can be moved out of and into a tubular guide using pneumatic means. Operation thereof requires the application of a pressure/vacuum system.

The greatest drawback of these endo-removal apparatuses is that the tissue that is extracted cannot be easily transported along other tissue. An opening must further be made in the thorax or abdominal wall for the organ or parts thereof to be removed, this opening being kept as small as possible to minimize the scarring to be left, and thereby facilitate the extraction. Some organs are also removed via a hollow organ which can be accessed from outside the body, such as the stomach, rectum, and vagina. It is nonetheless important that the tissue to be extracted have the smallest possible volume.

European Patent No. EP 959775 describes the use in an endo-removal apparatus of wires of spring steel inside a plastic bag parallel to the axis to enable cutting of the tissue into portions or compressing thereof. There is, however, a great risk of leakage of possibly malignant tissue fluid under such practices.

SUMMARY OF THE INVENTION

In view of the foregoing, the present invention has for a basic object to design an endo-removal apparatus or device 10 wherein the form of the tissue to be removed automatically takes up a position such that the cross-sectional diameter is as small as possible thereby to facilitate extraction. This implies that the axis of the tissue to be removed must run as parallel as possible to the tubular guide. In this latter position, a plastic bag slides easily along the organs, and the opening to be made in the stomach or abdominal wall is as small as possible. The endo-removal part will preferably further be both watertight and airtight and resistant to damage during the extraction of the tissue to be removed.

BRIEF DESCRIPTION OF THE DRAWINGS

The present invention is further elucidated with reference to the following drawings of the device for removing tissue according to the invention.

The figures are schematic and are not necessarily drawn to scale. Corresponding parts are designated in the figures with the same reference numerals.

DETAILED DESCRIPTION

One embodiment of the present invention takes the form of a device 10 comprising an operating part with a handle 1 and a partially open hollow tube with a guide 2 for operating a removing part 3 wherein the removing part has the form of a zeppelin with one or more ribs 6. This zeppelin form, which is as parallel as possible to the hollow tube, is advantageous as it takes up little space in the transport of removed tissue along other tissue, such as organs, and it can be easily pulled at least partially under or into the tubular guide. The removing part 3 can preferably be closed in an airtight and watertight manner to prevent leakage of possibly malignant tissue. The removing part 3 with the form of a zeppelin is more preferably provided for this purpose on the upper side thereof with longitudinal connecting elements 4. The connecting elements 4 can be of plastic or metal. One connecting element 4 can be provided with, for instance, thickened portions, and the other connecting element 4 can have corresponding recesses. These connecting elements 4 are preferably suitable for closing in accordance with a snap or zip principle.

In the removing part 3 of the device 10 according to the invention, one or more ribs 6 preferably run in a more or less oval shape in the longitudinal direction of the zeppelin-shaped removing part 3, and these ribs 6 more preferably run on into the optionally partially open, hollow tubular guide 2, 2'.

The removing part 3 with the form of a zeppelin of the device 10 according to the invention is preferably provided with a curved support 5 to facilitate pulling of this removing part 3 into the hollow tube 2, 2'. The curved support 5 can optionally have a lazy S-shape. The removing part 3 with the form of a zeppelin is preferably provided with a venting reservoir 9 with the purpose of preventing possibly imminent overpressure inside the removing part 3.

Figure 2A:
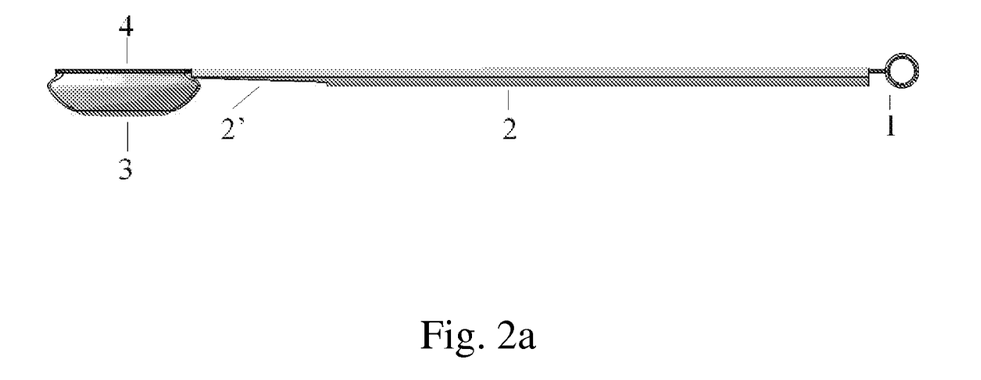
FIG. 2a is a view in side elevation of a device 10 pursuant to the invention comprising an operating part 1 with a hollow tube 2 that has a partially open portion 2' on its underside adjacent to the zeppelin-like removing part 3.
Figure 2B:
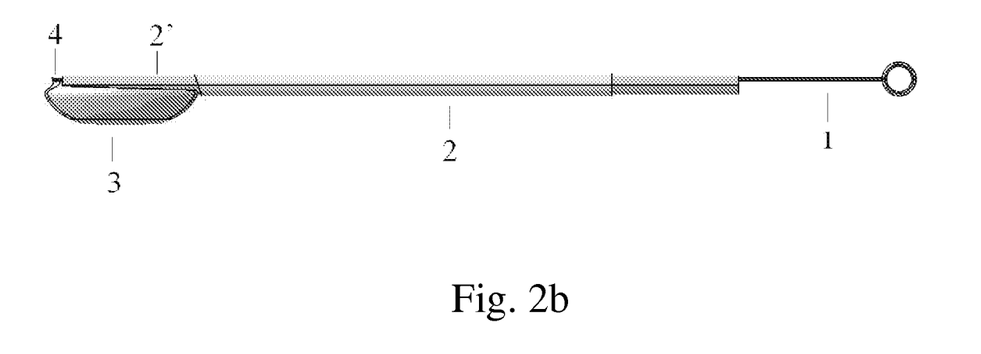
FIG. 2b is a view in side elevation of the device 10 comprising an operating part 1 with a hollow tube 2 with the partially open portion 2' on the underside adjacent to the zeppelin-like removing part 3 with the partially open portion 2' of the hollow tube 2 pushed over the removing part 4.
Figure 4:
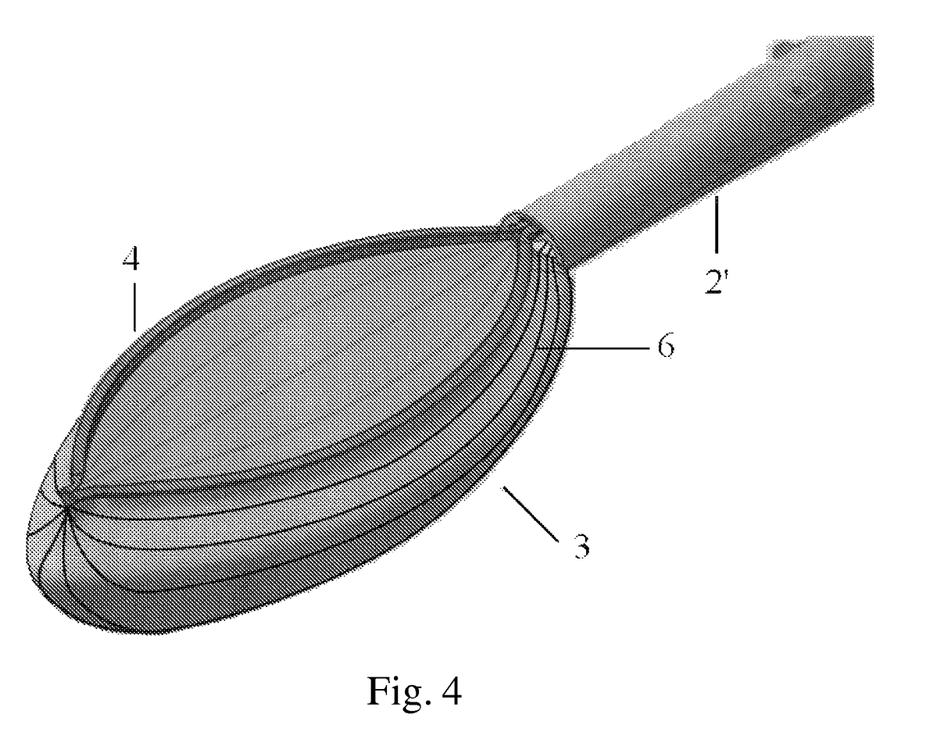
FIG. 4 is a perspective view of a device 10 according to the invention in the form of a zeppelin-shaped removing part 3 with spoon-like ribs running more or less parallel to connecting elements 4 and running on into the hollow tube 2.

Looking to FIGS. 2b and 4, the handle 1 of the operating part can be connected to one or more of the ribs 6 which run on into the partially open, hollow tube 2, wherein the ribs 6 can be pulled in during use in order to make the diameter of the zeppelin-shaped removing part 3 with the extracted tissue as small as possible. The handle 1 is connected to a closing mechanism for the connecting elements 4. When the handle 1 is also connected to one or more ribs 6, the removing part 3 can advantageously be closed during use in combination with a narrowing of the space between the ribs 6.

According to a first preferred embodiment of the invention, the hollow tube 2 is partially open on the underside on the side of the removing part 3 and is provided on the side of the removing part 3 with an opening in a form suitable for receiving both connecting elements 4 of the removing part.

Figure 5:
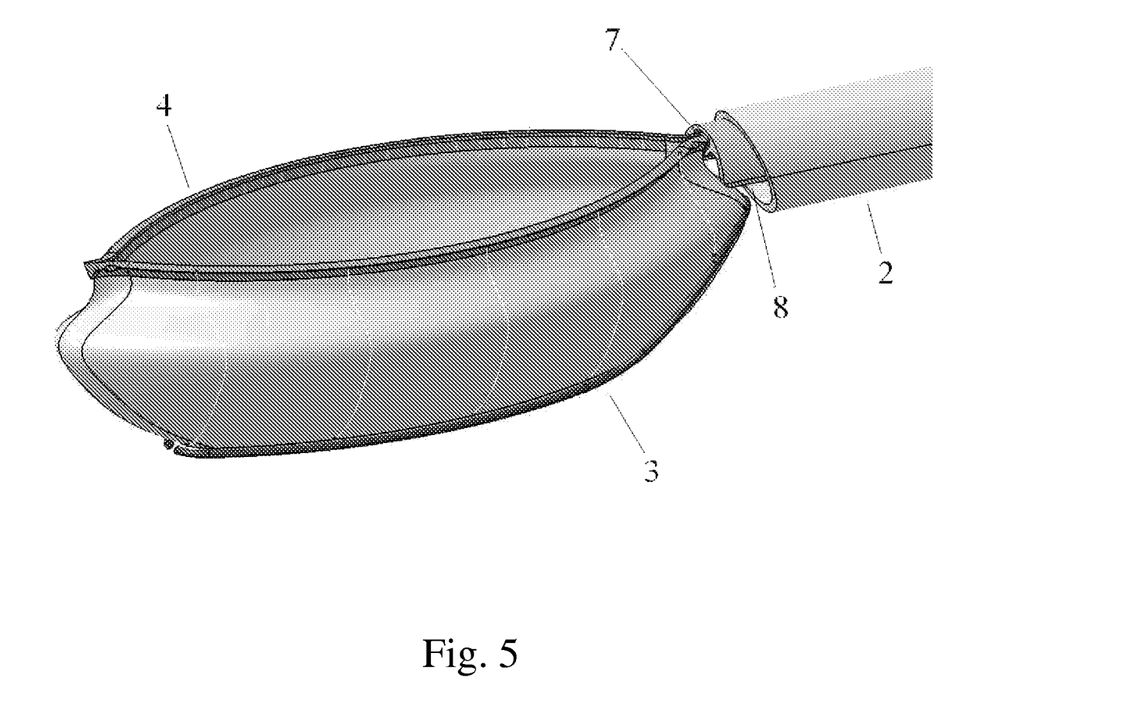
FIG. 5 is a perspective view of an alternative device 10 pursuant to the invention with a hollow tube 2 which is also closed on the underside, in which tube 2 is situated a rod 8 provided on the side of the removing part 3 with an opening 7 in a form suitable for receiving both connecting elements 4 of the zeppelin-like removing part 3.

According to a second preferred embodiment of the invention, the hollow tube 2 is closed. In the tube 2, a rod 8 is situated on the side of the removing part 3 as shown in FIG. 5 and is provided with an opening 7 in a form suitable for receiving both connecting elements 4 of the removing part 3.

Separately of the form of the removing part 3, the use of a hollow tube 2 which is optionally partially open on the underside in the transport of removed tissue is also new and particularly advantageous. Another aspect of the invention is therefore formed by the device 10 for removing tissue by means of laparoscopy or thoracoscopy, comprising an operating part with handle 1 and a hollow tube 2 with guide for operating a removing part 3, wherein a part of the hollow tube 2 is optionally partially open on the underside on the side of the removing part 3, and is provided on the same side with an opening 7 in a form suitable for receiving both connecting elements 4 of the removing part 3.

Another aspect of the invention is formed by applying the first preferred embodiment of the invention in a surgical treatment, wherein using the operating part the removing part 3 with the form of a zeppelin is opened out, the removed tissue is collected in the expanded removing part 3 and the removing part 3 with tissue is pulled at least partially into the open part of the hollow tube 2, wherein the connecting elements 4 of the removing part 3 are brought together, snapped or zipped closed.

Yet another aspect of the invention is formed by applying the second preferred embodiment of the invention in a surgical treatment, wherein using the operating part the removing part 3 with the zeppelin form is opened out and the rod 8 is pushed out, the removed tissue is collected in the expanded removing part 3, and the removing part 3 with tissue is pulled at least partially into the rod 8, wherein the connecting elements 4 of the removing part 3 are brought together, snapped or zipped closed.

The ribs 6 in the removing part 3 are preferably of plastic or light metal.

The connecting elements 4 preferably consist of plastic or metal flanges with a resilient action. They have a bias which ensures that they move apart as soon as they are pushed out of the tubular guide 2. When retracted, they are pressed together in the tubular guide 2 and they close the removing part 3. By means of being zipped or snapped shut, the flanges 4 can be closed with a closing mechanism so that separation of the flanges 4 during extraction can be prevented. The flanges 4 can be provided for this purpose at the outer end with a thickened portion and a recess there behind with a configuration such that, after closing of the zeppelin-shaped removing part 3, this closure is anchored and fully closed so that no further separation can take place. Other configurations for closure of the flanges 4 with toothing are also possible. The two connecting elements 4, such as flanges 4, can also be identical and be brought together in the hollow tube 2 or in the rod 8 present in the hollow tube 2. The material of which the zeppelin-like removing part 3 according to the invention consists is not critical, but will preferably be watertight and airtight; in the first instance flexible material, such as plastic or another flexible synthetic material, is suitable.

When applying the partially open, hollow tube 2 or half-open tube 2 of the first embodiment of the invention, it is also possible and advantageous to close the removing part 3 by sliding this half-open tube 2 over the connecting elements 4. The zeppelin-like configuration of the removing part 3 with an oval shape in the horizontal plane and a lazy S-shape in the vertical plane makes extending of the removing part 3 in the tube 2 possible during closing.

The rod 8 of the second embodiment of the invention must have a form such that it fits in the hollow tube 2 and is provided with an additional tubular open space, generally forming part of the open space of the hollow tube 2. The opening of the open space of the rod 8 has a shape suitable for receiving both connecting elements 4 of the removing part.

In both depicted embodiments of the invention, it is recommended to retract the removing part 3 into the tubular guide 2 by pulling on the ribs 6. This can, for instance, be realized by arranging an instrument that is connected to the ribs 6 and pulling on them. By way of example, this could be accomplished through a turn-buckle on the outer end of the hollow tube 2 whereby the removing part 3 can be retracted into the rod 8 or partially open hollow tube 2.

Figure 1:
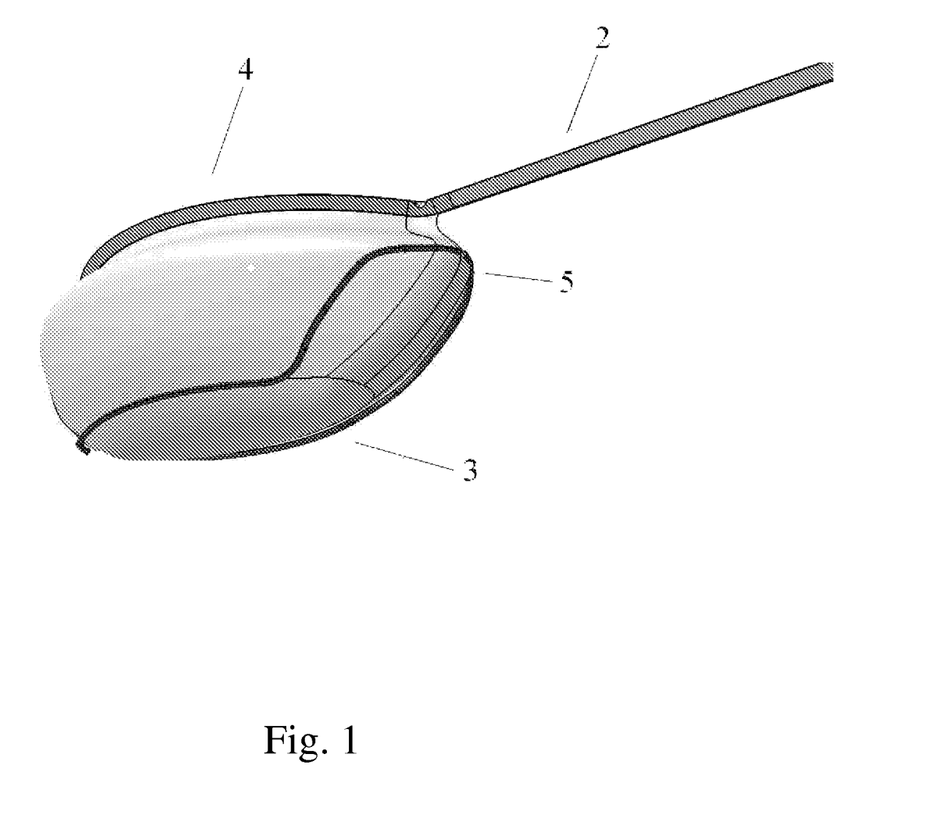
FIG. 1 is a perspective view of a device 10 according to the invention with a hollow tube guide 2 for operating a removing part 3 in the form of a zeppelin with one or more ribs, connecting elements 4, and an S-shaped support 5.

As used herein, the form of a zeppelin for the removing part 3 is to be understood to mean slightly more than the lower half of a zeppelin airship and as shown in FIGS. 1-5 and 9. This configuration of the removing part 3 can also be designated in the open position as the form of a scoop or convex spoon, which can also be advantageously obtained when a plurality of ribs 6 run more or less ovally in the longitudinal direction of the zeppelin form of the removing part 3 or, in other words, more or less parallel to the connecting elements 4, which ribs 6 have a bias and take the form of a scoop or spoon when the removing part 3 is opened out, as shown perhaps most clearly in FIG. 4. With the S-shaped or lazy S-shaped support 5, this rib is indicated in the form as shown in FIG. 1 wherein the S-shape is visible on the long side of the zeppelin-shaped removing part 3.

The zeppelin-shaped removing part 3 with ribs can also be envisaged as a cage with flexible bars in which the tissue for removal is safely packaged and transported either into the hollow tubular guide 2 partially open on the underside or into the closed hollow tubular guide 2.

The terms tubular guide 2 and tube with guide 2 are used as synonyms in the present patent application. In the present patent application, a partially open hollow tube 2 is understood to mean a hollow tube 2 which, at least during use, has on the underside an open part situated to the side of the removing part 3. An optionally partially open hollow tube 2 is also understood to include the possibility of a closed hollow tube 2.

In this patent application, tissue is understood to mean human or animal material or fluids, such as organs or blood and other bodily fluids. The tubular guide 2 as part of the device 10 according to the invention can also comprise a trocar.

FIG. 1 shows an oblique detail front view of the removing part 3 in the form of a zeppelin with one or more ribs, connecting elements 4 and an S-shaped support 5. The ribs and S-shaped support 5 impart shape and support to the removing part 3 and facilitate the possible partial retraction of the removing part 3 into the tube 2. FIGS. 2a and 2b show two positions of the first embodiment of the device 10 according to the invention, wherein the tubular guide 2 comprises an opening 2' which is open on the underside. Once the tissue to be removed has been received in the zeppelin-like removing part 3, the opening 2' is pushed over this removing part 3 as shown in FIG. 2b such that the remaining portion of the tube 2 overlies the removing part 3. The opening 2' on the underside of the part of the hollow tube 2 which is partially open tapers if necessary to realize the most efficient possible closure of the removing part 3.

Figure 3:
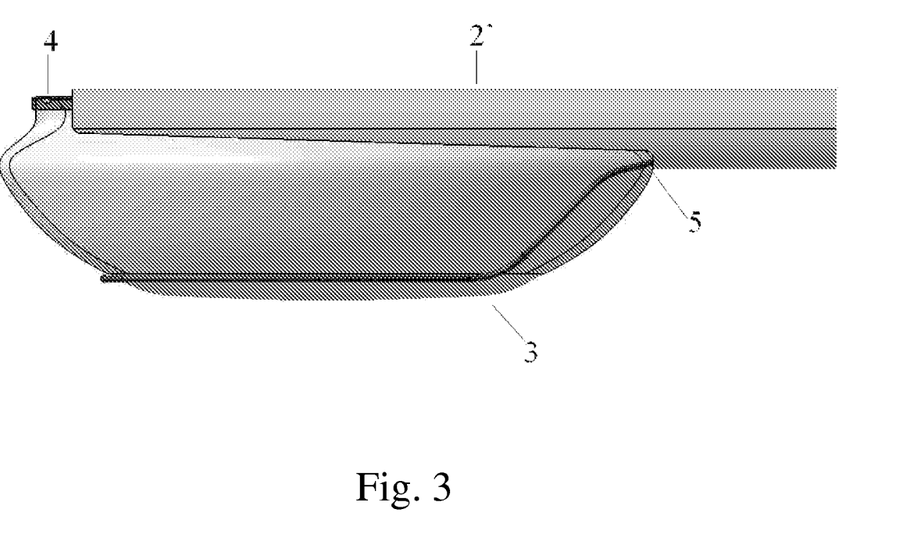
FIG. 3 is an enlarged view in side elevation of the removing part 3 of FIG. 2b in the form of a zeppelin with ribs, closed connecting elements 4, and an S-shaped support, wherein the open part of the hollow tube 2' has been pushed over the removing part 4.

The opening part 2' is shown enlarged in FIG. 3. The ribs on the rear side of the removing part 3 are preferably already situated partially in the tubular guide 2 of the first embodiment or in the rod 8 of the second embodiment of the invention. With that, as the tube 2 is pushed further forward, the ribs are forced to move further inward. Also, due to the curved form of supporting ribs, the removing part 3 will be urged partially or wholly upward in the tube 2 or rod 8 as in FIG. 5, and the removing part 3 will be compressed on the underside in the tube 2 or rod 8.

FIG. 4 shows the removing part 3 in the expanded form in a further preferred embodiment of the first embodiment of the device 10 according to the invention, i.e. in zeppelin-shaped removing part 3 with ribs in the longitudinal direction more or less parallel to the connecting elements and the open part 2' of the hollow tube into which the ribs run. An embodiment with a removing part 3 with the same form of ribs, but then applied in the second embodiment of the invention with a closed hollow tube 2, otherwise also forms part of the present invention.

FIG. 5 shows the tubular guide 2 and the removing part 3 of the second embodiment of the device 10 according to the invention wherein present in the hollow tubular guide 2 is a rod 8 which, once the tissue to be removed has been received in the zeppelin-like removing part 3, can be pushed over this removing part 3. The rod 8 comprises for this purpose an opening 7 with a form suitable for receiving the connecting elements 4. When this rod 8 is pushed over the connecting elements 4, they are for instance snapped or zipped together, whereby the removing part 3 is closed.

Figure 6:
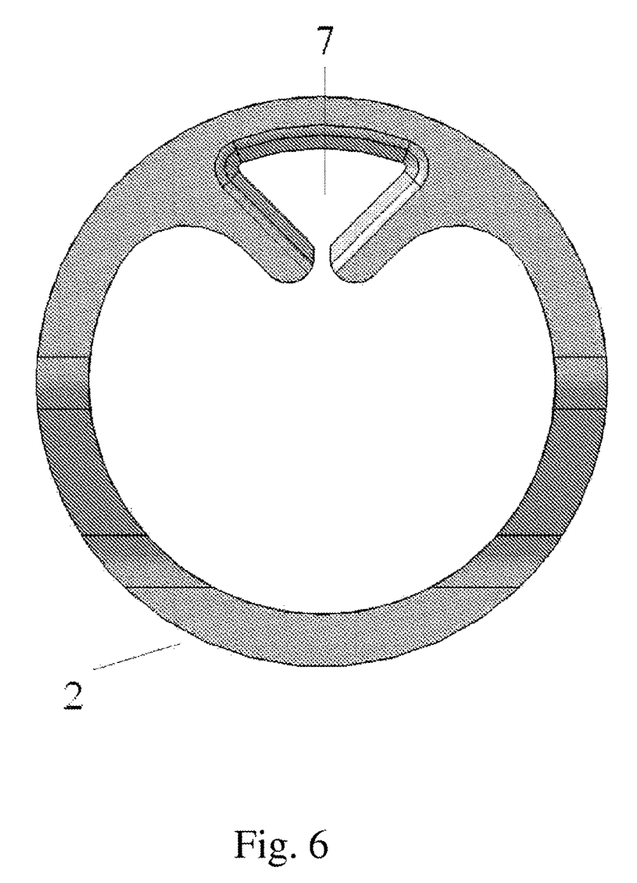
FIG. 6 is a cross-sectional view of a part of the device 10 according to the invention with a hollow tube 2 closed on the underside and with an opening 7.

FIG. 6 shows such an opening 7 in a form suitable for collecting or receiving the two connecting elements 4 of a removing 3 part as shown for instance in FIG. 5.

Figure 7:
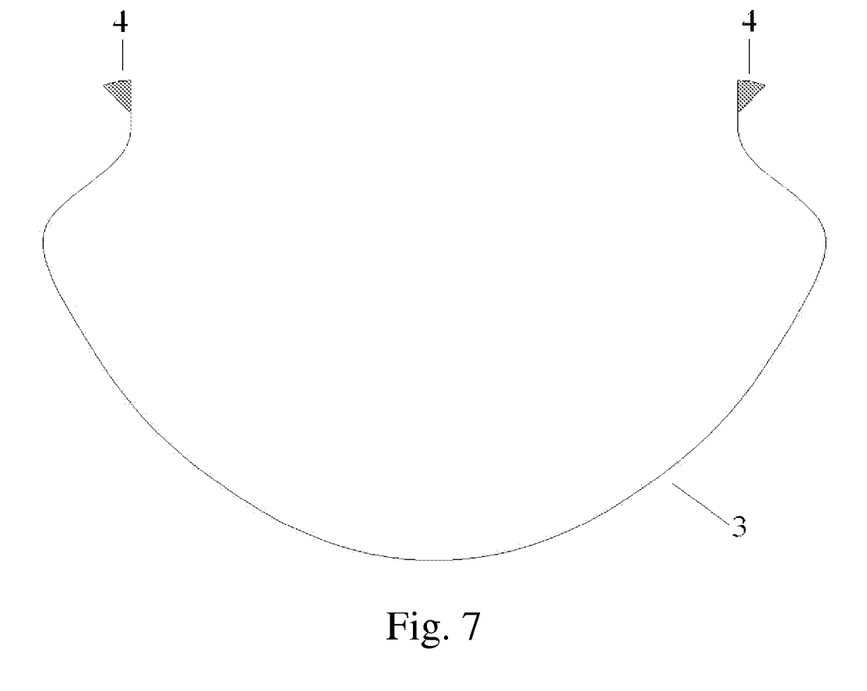
FIG. 7 is a cross-sectional view of a zeppelin-like removing part 3 of a device according to the invention with connecting elements 4 in an open position.
Figure 8:
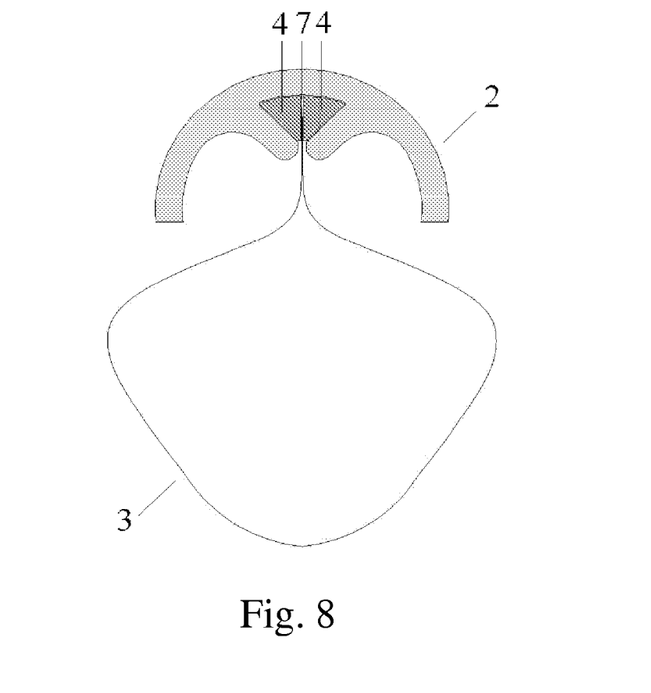
FIG. 8 is a cross-sectional view of a zeppelin-like removing part 3 of a device according to the invention with connecting elements 4 in a closed position in opening 7 of the hollow tube 2 optionally open on the underside.
Figure 9:
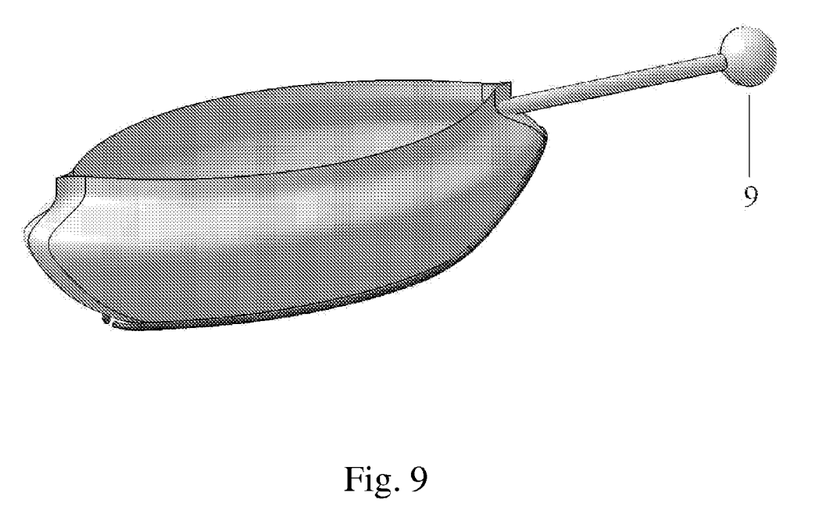
FIG. 9 is a perspective view of the removing part 3 with the form of a zeppelin provided with a venting reservoir 9.

FIGS. 7 and 8 show respectively the open and closed form of the removing part 3 of the device 10 according to the invention. Able to serve as connecting elements 4 are for instance flanges of plastic which in closed position of the removing part 3 are received in the opening 7 of suitable form. FIG. 9 shows the removing part 3 with the form of a zeppelin provided with an example of a venting reservoir 9 with the purpose of preventing imminent overpressure inside the removing part 3. The venting reservoir 9 preferably protrudes from the removing part 3 into the tubular guide 2, from which it can be operated.

It will be apparent to the person with ordinary skill in the art that the present invention provides a new endo-removal apparatus 10 in different embodiments which provides a great advantage relative to the existing endo-removal apparatuses, including safer removal and transport of tissue by means of laparoscopy or thoracoscopy than is possible with heretofore known endo-removal apparatuses.

Although the invention is elucidated above on the basis of different embodiments and applications, it will be apparent that the invention is by no means limited thereto. On the contrary, many more variations are possible for a person with ordinary skill in the art within the scope of the invention.

The invention claimed is:

1. A device for removing tissue by means of laparoscopy or thoracoscopy, the device comprising a hollow tube with a proximal end, a distal end, and a longitudinal portion between the proximal and distal ends, an operating part with a handle retained by the hollow tube, and a removing part comprising a bag of flexible, watertight material retained adjacent to the distal end of the hollow tube wherein the distal end of the hollow tube has an opening for receiving the bag of the removing part, wherein the hollow tube has a guide for operating the removing part and wherein the bag of the removing part has the form of a zeppelin and further comprising first and second longitudinal connecting elements disposed along an upper side of the bag of the removing part and a plurality of ribs wherein the plurality of ribs run in a substantially oval shape in a longitudinal direction of the bag of the removing part wherein the handle is connected to a closing mechanism of the connecting elements and wherein the hollow tube is partially open along a distal segment of the longitudinal portion along an underside thereof adjacent to the removing part.

2. The device of claim 1, wherein the removing part can be closed in an airtight and watertight manner.

3. The device of claim 1, wherein the connecting elements are of plastic or metal.

4. The device of claim 1, wherein the removing part further comprises a curved supporting rib wherein the supporting rib is generally S-shaped.

5. The device of claim 1, wherein the removing part further comprises a venting reservoir.

6. The device of claim 1, wherein the handle of the operating part is connected to the ribs and wherein the ribs pass into the hollow tube.

7. The device of claim 1, wherein the distal end of the hollow tube has a sub-opening adjacent to the removing part for receiving the connecting elements, wherein the sub-opening is contiguous with the opening for receiving the bag of the removing part, and wherein the operating part is operative to pull the removing part into the opening and the connecting elements into the sub-opening.

8. The device of claim 1 wherein the plurality of ribs are formed from plastic or metal.

9. A device for removing tissue by means of laparoscopy or thoracoscopy, the device comprising a hollow tube with a proximal end, a distal end, and a longitudinal portion between the proximal and distal ends, an operating part with a handle retained by the hollow tube, and a removing part comprising a bag of flexible, watertight material retained adjacent to the distal end of the hollow tube wherein the distal end of the hollow tube has an opening for receiving the bag of the removing part, wherein the hollow tube has a guide for operating the removing part and wherein the bag of the removing part has the form of a zeppelin and further comprising first and second longitudinal connecting elements disposed along an upper side of the bag of the removing part and a plurality of ribs wherein the plurality of ribs run in a substantially oval shape in a longitudinal direction of the bag of the removing part wherein the handle is connected to a closing mechanism of the connecting elements and a rod retained by the hollow tube, wherein the rod is disposed adjacent to the removing part, and wherein the rod has a sub-opening for receiving both connecting elements of the removing part wherein the sub-opening is contiguous with the opening for receiving the bag of the removing part.

10. A device for removing tissue by means of laparoscopy or thoracoscopy, the device comprising a hollow tube with a proximal end, a distal end, and a longitudinal portion between the proximal and distal ends, an operating part with a handle retained by the hollow tube, a removing part comprising a bag retained adjacent to the distal end of the hollow tube wherein the distal end of the hollow tube has an opening for receiving the bag of the removing part, first and second longitudinal connecting elements connected to the bag, wherein the hollow tube has a guide for operating the removing part, wherein a sub-opening is disposed at the distal end of the hollow tube for receiving the connecting elements, wherein the sub-opening is contiguous with the opening for receiving the bag of the removing part, and wherein the operating part is operative to pull the bag of the removing part into the opening and the connecting elements into the sub-opening.

11. A method for using the device of claim 10 in a surgical treatment, the method comprising using the operating part to open the removing part outwardly, collecting removed tissue in the opened removing part, and pulling the removing part with tissue at least partially into the opening disposed at the end of the hollow tube to bring the connecting elements of the removing part together.

12. A method for using the device of claim 10 in a surgical treatment, wherein the device further comprises a rod retained by the hollow tube, wherein the rod is disposed adjacent to the removing part, and wherein the sub-opening is disposed in the rod for receiving both connecting elements, the method comprising using the operating part to open the removing part thereby pushing the rod out, collecting removed tissue in the removing part, and pulling the removing part with the removed tissue therein at least partially into the rod to bring the connecting elements of the removing part together.

13. The method of claim 12, wherein the connecting elements are snapped or zipped closed.

\* \* \* \* \*